United States Patent [19]
Gershony et al.

[11] Patent Number: 5,626,601
[45] Date of Patent: May 6, 1997

[54] VASCULAR SEALING APPARATUS AND METHOD

[75] Inventors: Gary Gershony, 44332 S. El Macero Dr., El Macero, Calif. 95618; Daniel J. Kasprzyk, Fogelsville, Pa.; Michael J. Horzewski, San Jose, Calif.

[73] Assignee: Gary Gershony, El Macero, Calif.

[21] Appl. No.: 549,332

[22] Filed: Oct. 27, 1995

[51] Int. Cl.⁶ .................................................. A61M 29/00
[52] U.S. Cl. .......................... 606/194; 604/101; 604/96
[58] Field of Search ................... 606/191, 192, 606/194, 195, 198, 213; 623/1, 12; 604/96, 101

[56] References Cited

U.S. PATENT DOCUMENTS

| | | |
|---|---|---|
| 2,862,497 | 12/1958 | Pagano . |
| 4,555,242 | 11/1985 | Saudagar . |
| 4,701,163 | 10/1987 | Parks . |
| 4,738,658 | 4/1988 | Magro et al. . |
| 4,852,568 | 8/1989 | Kensey . |
| 4,890,612 | 1/1990 | Kensey . |
| 5,021,059 | 6/1991 | Kensey et al. . |
| 5,042,985 | 8/1991 | Elliott et al. . |
| 5,053,046 | 10/1991 | Janese . |
| 5,061,274 | 10/1991 | Kensey . |
| 5,108,421 | 4/1992 | Fowler . |
| 5,129,882 | 7/1992 | Weldon et al. . |
| 5,159,937 | 11/1992 | Tremulis . |
| 5,176,692 | 1/1993 | Wilk et al. . |
| 5,222,974 | 6/1993 | Kensey et al. . |
| 5,246,421 | 9/1993 | Saab ............................................ 604/96 |
| 5,250,025 | 10/1993 | Sosnowski et al. . |
| 5,328,471 | 7/1994 | Slepian ..................................... 604/101 |
| 5,383,896 | 1/1995 | Gershony et al. . |
| 5,486,195 | 1/1996 | Myers et al. . |

FOREIGN PATENT DOCUMENTS

| | | |
|---|---|---|
| 0416734A1 | 3/1991 | European Pat. Off. . |
| 9000078 | 12/1990 | WIPO . |
| 9201418 | 12/1992 | WIPO . |

*Primary Examiner*—Michael Buiz
*Assistant Examiner*—Kevin Truong
*Attorney, Agent, or Firm*—Townsend and Townsend and Crew LLP

[57] ABSTRACT

A vascular sealing device for effecting closure of a puncture or other opening in a blood vessel, or other body cavity, which has been entered through percutaneous techniques. The device is useable with a standard percutaneous vascular introducer. The vascular sealing device generally comprises a body or shaft, an adapter disposed at a proximal end of the shaft, and a balloon portion disposed generally at a distal end of the shaft. A core wire is connected to the distal end and extends, internally, through a lumen of the device for deflation of the balloon. A procoagulant is introduced through the introducer, or alternatively through an additional lumen and associated apertures, and to the puncture sealed by the inflated balloon. Subsequently, the balloon is deflated and the device is removed from the sealing puncture, with or without the aid of a reaccess sheath.

21 Claims, 4 Drawing Sheets

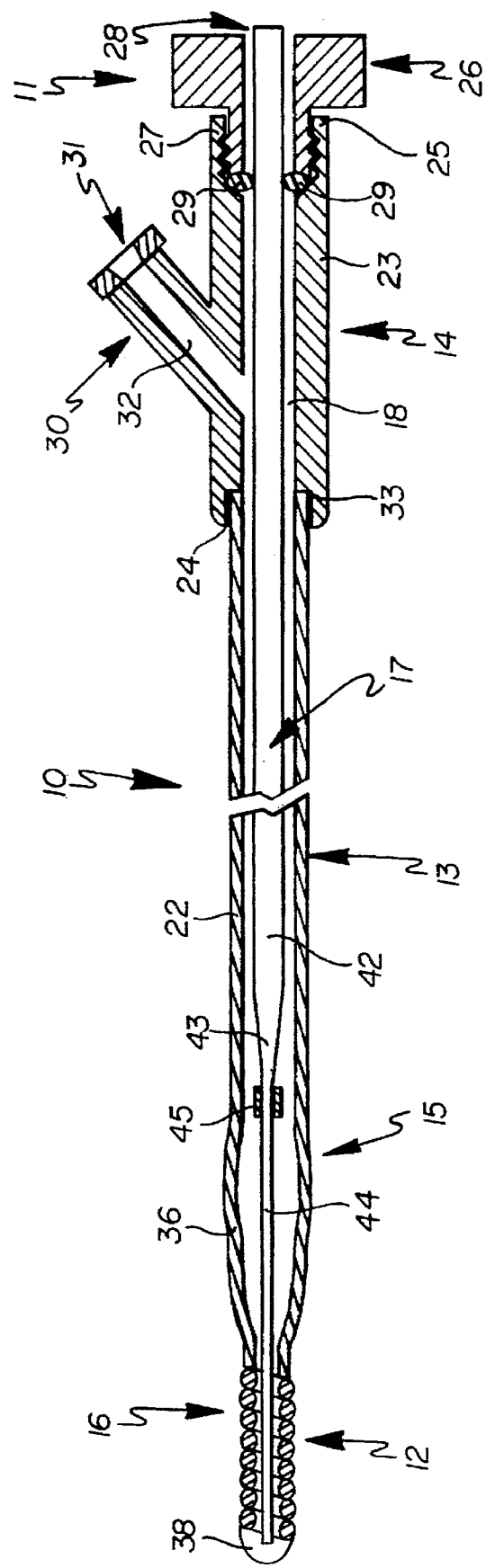
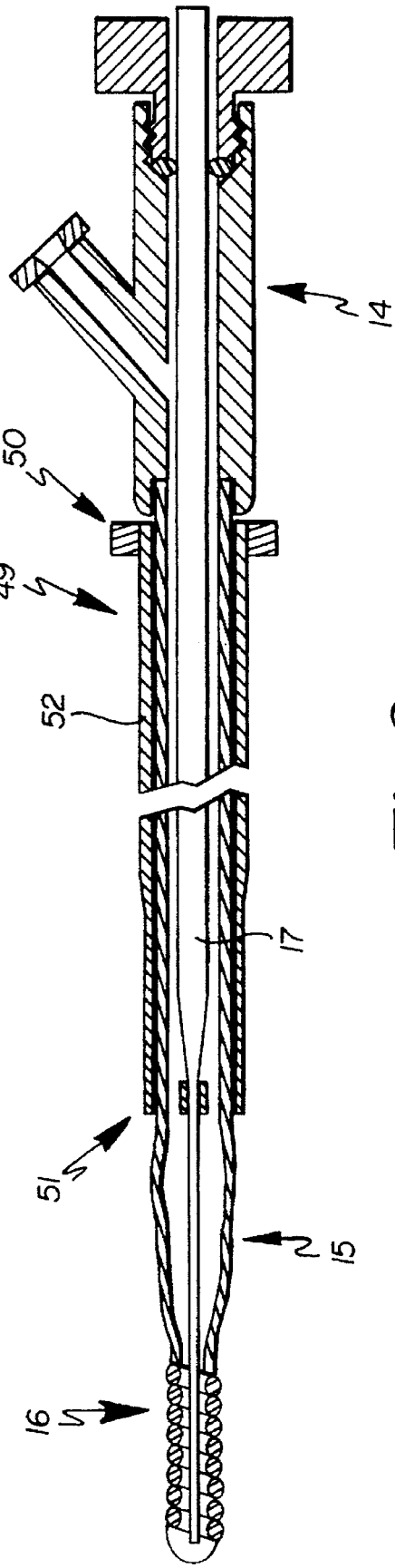
Fig. 1
Fig. 2

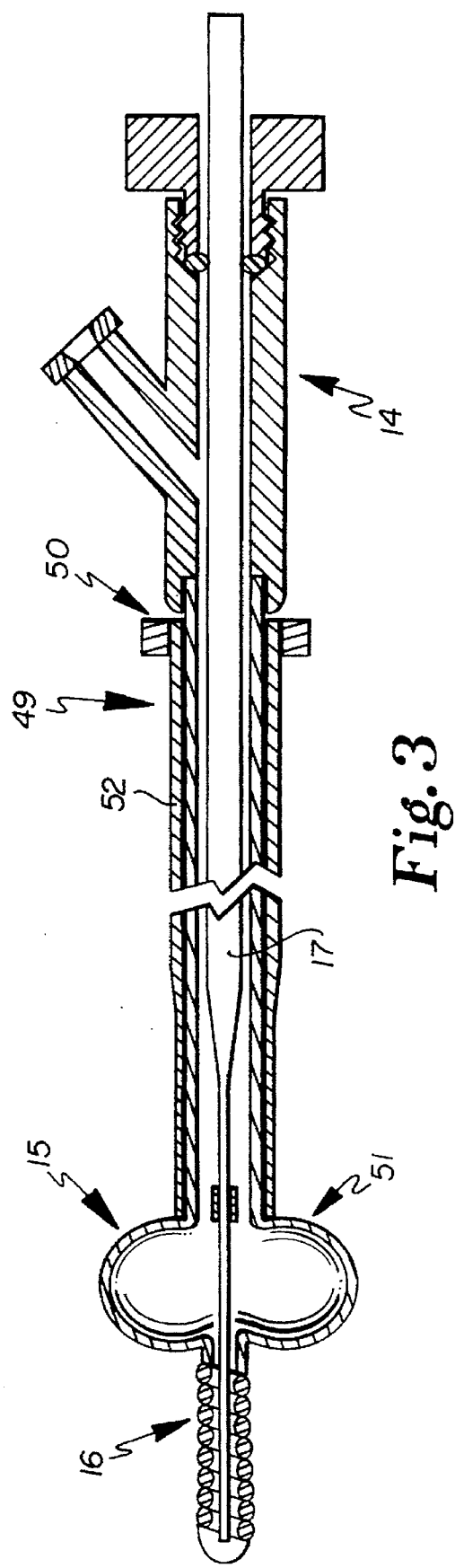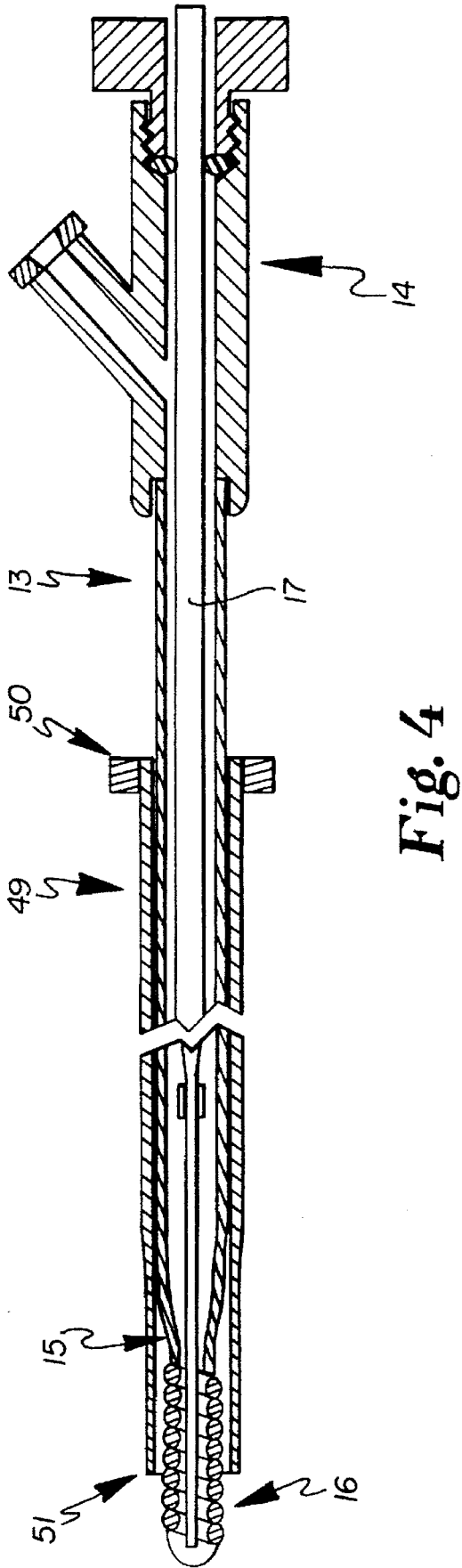

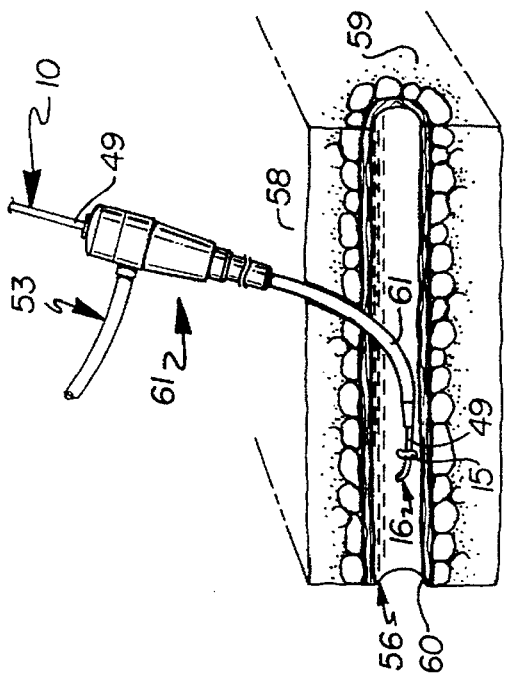
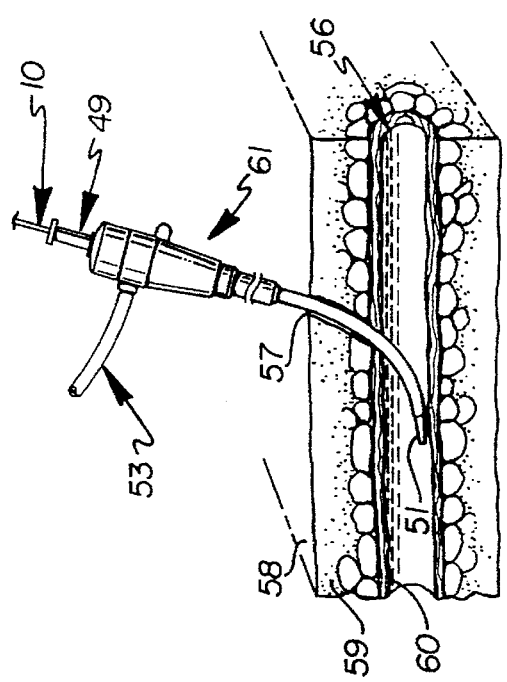
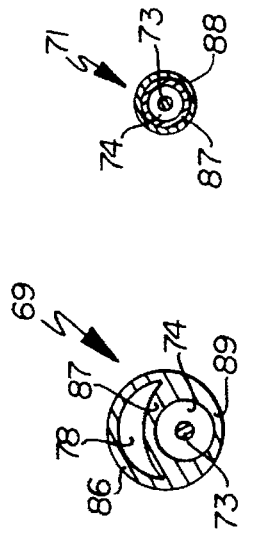
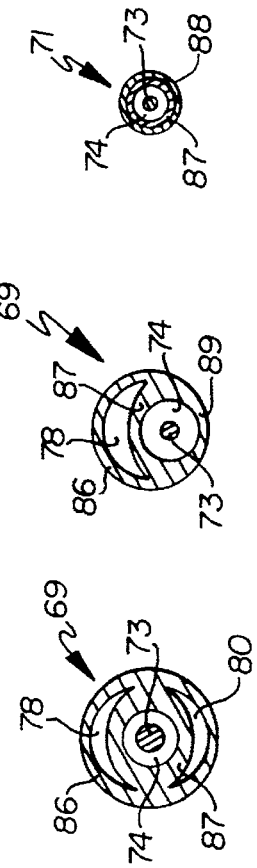
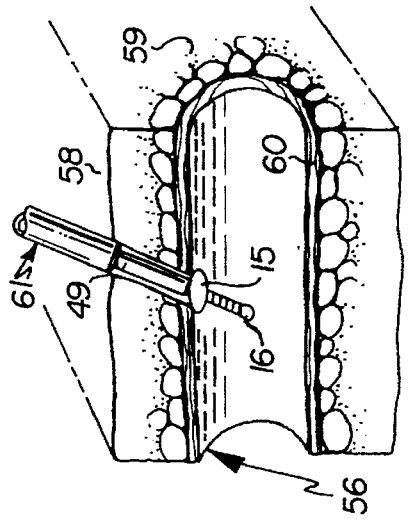

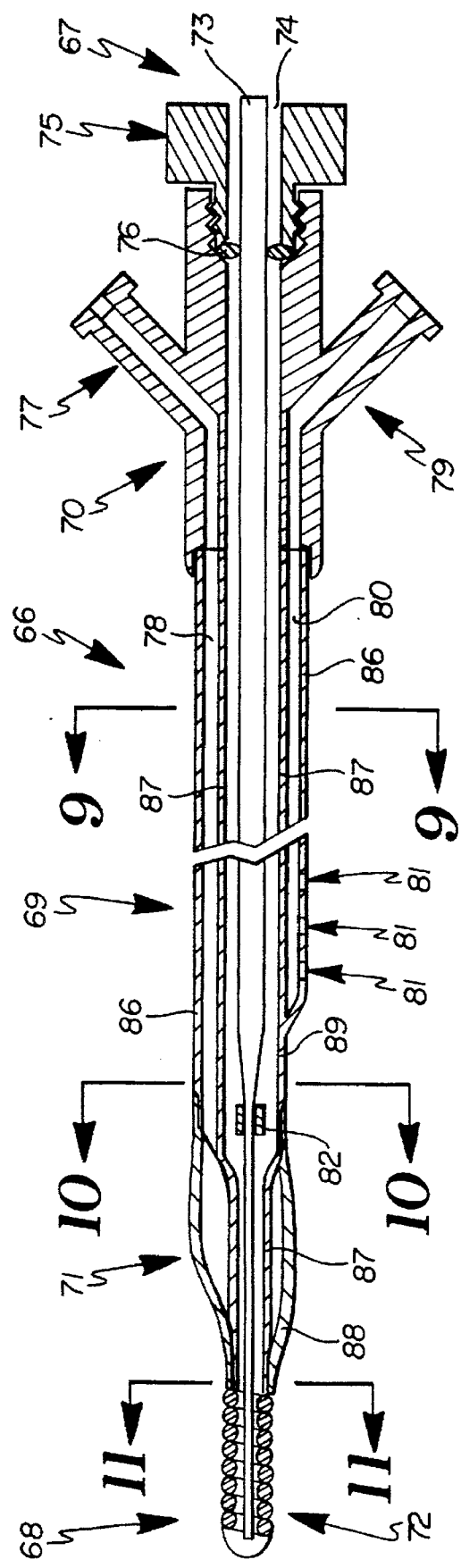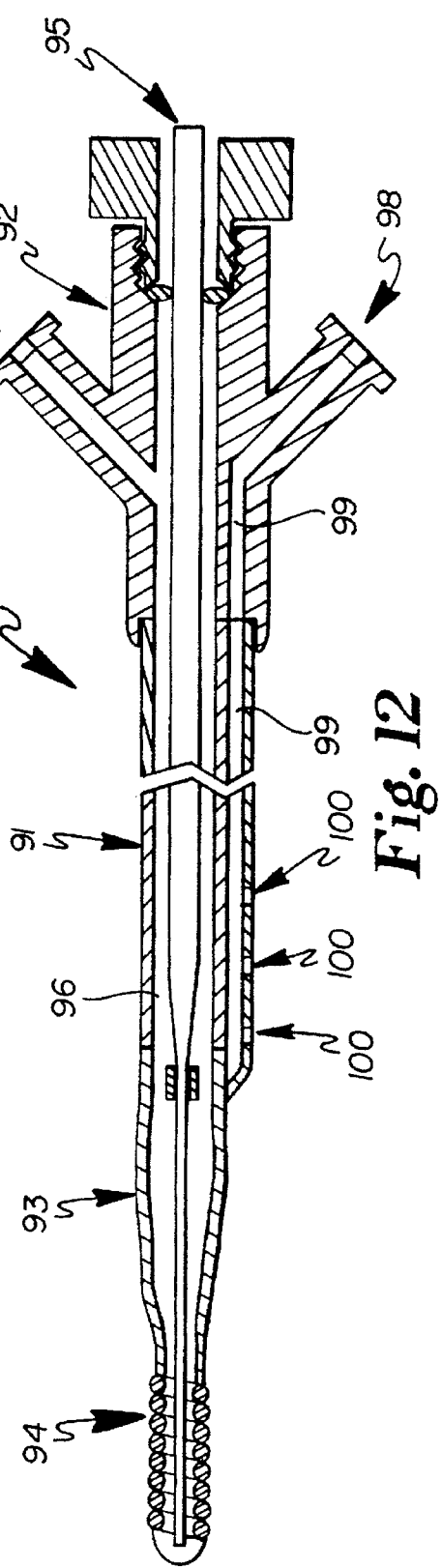
Fig. 8
Fig. 12

VASCULAR SEALING APPARATUS AND METHOD

BACKGROUND OF THE INVENTION

1. Field of the Invention.

This invention relates, generally, to medical devices. More particularly, the invention relates to hemostatic devices used for arresting the flow of blood or hemorrhage from punctures of the vascular system.

2. Background Information.

Various surgical procedures are performed by medical specialists such as cardiologists and radiologists utilizing percutaneous entry into a blood vessel or body cavity. Examples of such procedures include different techniques to recanalize atherosclerotic blood vessels, such as balloon angioplasty or atherectomy. Recently, both the types and number of procedures performed utilizing the above mentioned percutaneous access to blood vessels have increased greatly.

These procedures generally involve the percutaneous puncture with a thin walled needle into a blood vessel. Following this, a guidewire is placed through the needle into the blood vessel and the needle is withdrawn. An intravascular sheath of variable size is then advanced over the guidewire, percutaneously, into the lumen of the blood vessel. The introducer sheath is then used as an ingress/egress means during the procedure. Following completion of the procedure, the introducer sheath may be removed, but this requires the application of prolonged manual pressure over the puncture site by a physician or other suitably trained medical personnel. The time involved here is frequently extensive since patients are often treated with a variety of anticoagulant and thrombolytic agents, particularly in the setting of a heart attack. Alternatively, the sheath may be left in the puncture site for a prolonged period of time until the patient's coagulation status has returned to normal. Depending on the size of the vascular sheath, there may be an increased risk of bleeding to the patient, which may require blood transfusion. In addition, there is a significant risk for injury to the blood vessel upon removal of the sheath, particularly if the sheath has been in place for a prolonged period of time. This includes the possible development of an pseudo-aneurysm or severe hematoma. The current technique for removal of introducer sheaths is also painful to the patient and requires prolonged bed rest after removal. This adds to the discomfort for the patient, as well as prolonging hospitalization and costs.

Many of the intra-vascular procedures are performed in patients who are clinically unstable or who have the potential to become so, following completion of the procedure. Following removal of the vascular access sheath, it could be cumbersome and sometimes difficult to re-enter the blood vessel if necessary. Thus, with the current technique for removal of the sheath following the procedure, no easy, reliable method is available to allow reaccess to the lumen of the blood vessel, unnecessary.

The prior art includes U.S. Pat. No. 4,744,364 to Kensey, U.S. Pat. No. 4,852,568 to Kensey, and U.S. Pat. No. 4,890,612 to Kensey, which disclose a method and device for sealing punctures in blood vessels by injection of a resorbable hemostatic plug into the puncture site. These devices and methods have a number of shortcomings and problems. U.S. Pat. No. 5,383,896 to Getsbony et al. discloses a vascular sealing device having a thin conduit with a baboon at a distal end and an elastomeric seal at a proximal end.

Despite the need for a device and method in the an which overcomes the limitations and problems of the prior art, none insofar as is known has been proposed or developed.

SUMMARY OF THE INVENTION

This invention provides a vascular sealing device for effecting closure of a puncture or other opening in a blood vessel, or other body cavity, which has been entered through percutaneous techniques. The device is useable with a standard percutaneous vascular introducer. The vascular sealing device generally comprises a body or shaft, an adapter disposed at a proximal end of the shaft, and a baboon portion disposed generally at a distal end of the shaft. A core wire is connected to the distal end and extends, internally, through a central lumen of the device for deflation of the balloon. A procoagulant is introduced through the introducer, or alternatively through an additional lumen and associated apertures, and to the puncture sealed by the inflated balloon. Subsequently, the baboon is deflated and the device is removed from the sealing puncture, with or without the aid of a reaccess sheath. A method of sealing a puncture site is also disclosed and claimed.

In one embodiment, the medical sealing device body structure adapter has an inflation port communicatively connected to the central lumen. The central lumen is communicatively connected to the inflation member, whereby fluid is introduced in the inflation port and through the central lumen to inflate the inflation member. In this embodiment, the means to introduce a procoagulant is an introducer having an axial lumen opening to a distal insertion end adapted for location in the blood vessel opening, a fluid injection port being communicatively connected to the introducer lumen, the body structure shaft being extended through the introducer lumen so that the inflatable member is disposed outwardly beyond the introducer distal insertion end, procoagulant being introduced to the introducer lumen via the fluid injection port and distributed out the distal insertion end.

In a second embodiment, the medical sealing device body structure adapter has an inflation port and a communicatively connected longitudinal inflation lumen. The inflation lumen is communicatively connected to the inflation member, whereby fluid is introduced in the inflation port and through the inflation lumen to inflate the inflation member. In this embodiment, the means to introduce a procoagulant comprises a procoagulant introduction lumen disposed within the body structure, a procoagulant ingress port disposed on an exterior surface of the body structure and being communicatively connected to the introduction lumen, and at least one procoagulant egress aperture disposed at a predetermined location on the body structure and being communicatively connected to the introduction lumen.

In a third embodiment, the medical sealing device of claim body structure adapter has an inflation port communicatively connected to the central lumen. The central lumen is communicatively connected to the inflation member, whereby fluid is introduced in the inflation port and through the central lumen to inflate the inflation member. In this embodiment, the means to introduce a procoagulant also comprises a procoagulant introduction lumen disposed within the body structure.

Unique aspects of this invention include: (1) the creation of immediate hemostasis at the puncture site for procoagulant delivery; (2) the device baboon acts as a marker for delivery of procoagulant; (3) balloon approach prevents injection of procoagulant into the bloodstream; (4) baboon shape is controllable and blood vessel occlusion is minimized; (5) the balloon has a low profile for placement and removal; and (6) the apparatus and method allow reaccess to the patient's vasculature. Other features, benefits and objects of this invention will become clear from the following description by reference to the drawings.

BRIEF DESCRIPTION OF THE DRAWINGS

FIG. 1 is an axial, crossectional view, broken longitudinally, of the vascular sealing device of the present invention, in a normal, uninflated state.

FIG. 2 is an axial, crossectional view, broken longitudinally, of the vascular sealing device, in an uninflated state and disposed in an operative orientation through a standard access sheath.

FIG. 3 is a crossectional view of the vascular sealing device shown in FIG. 2, in an inflated state.

FIG. 4 is a crossectional view of the vascular sealing device shown in FIG. 1, in an uninflated state and partially retracted through the vascular access sheath.

FIG. 5 is a view of the vascular sealing device inserted through an introducer sheath and into a patient's vascular system, which is shown enlarged and in section.

FIG. 6 is a view of the vascular sealing device inserted through a vascular introducer or sheath, and being inflated.

FIG. 7 is a view of the vascular sealing device with its balloon portion inflated, and further showing retraction of the vascular introducer.

FIG. 8 is an axial, crossectional view of an alternative embodiment of the vascular sealing device of the present invention.

FIG. 9 is a crossectional view of the vascular sealing device shown in FIG. 8, taken along line 9—9 thereof.

FIG. 10 is a crossectional view of the vascular sealing device taken along line 10—10 of FIG. 8.

FIG. 11 is a crossectional view of the vascular sealing device taken along line 11—11 of FIG. 8.

FIG. 12 is an axial, crossectional view of yet another alternative embodiment of the vascular sealing device of the present invention.

DESCRIPTION OF THE PREFERRED EMBODIMENTS

FIG. 1 shows a preferred embodiment of the vascular sealing device 10 for effecting closure of a puncture or other opening in a blood vessel which has been entered through percutaneous techniques. The device 10 is useable with a standard percutaneous vascular sheath or introducer. The vascular sealing device 10 has proximal 11 and distal 12 ends. The vascular sealing device 10 generally comprises a body or shaft 13, an adapter or hub 14 disposed at the proximal end of the shaft 13, a balloon 15 portion disposed at the distal end of the shaft 13, and a tip 16 disposed at the distal end of the balloon 15. A core wire 17 is connected to the tip 16 and extends, internally, through a lumen 18 of the device 10. Basically, the proximal end 11 of the device 10 is for manipulation, inflation, and connection to associated medical apparatus described further below, while the distal end 12 is for insertion into the patient's body.

The shaft 13 is rigid and has an elongated cylindrical or tubular configuration. The shaft 13 has a diameter less than the diameter of the access lumen of the introducer or sheath with which it is used, and a predetermined length at least two (2) cm. greater than that of the introducer. Thus, for example for a standard 12 cm. introducer, the shaft 13 would be at least 14 cm. long. A hollow center or lumen 18 extends the entire length of the shaft 13. The proximal end of the shaft 13 is connected to the hub 14 as is described below. The distal end of the shaft 13 is connected to the balloon 15 via heat bonding, an adhesive or other known means. The shaft 13 may be constructed of HDPE, polyimide, nylon, stainless steel, or a combination of such materials, for example.

The hub 14 provides a means of inflating the balloon 15, a means of access to lumen 18, and a means of permitting the movement of core wire 17 while simultaneously preserving the sealed environment of lumen 18. The hub 14 is rigid and has an generally cylindrical configuration. The hub 14 has a body 23 with an integral inflation port arm 30. A hollow center or lumen extends from the proximal end of the hub 14, axially and distally, to communicatively connect with the lumen 18 of the shaft. The inflation port arm 30 is disposed at an angle with respect to the hub body 23 and has a lumen 32 which is communicatively connected to the hub lumen. The arm 30 has an inflation port 31 disposed at its extended end. Preferably, the port 31 has a connector such as a Luer-Lock connector for mating with an inflation device (not shown) as is know in the art. Upon connection of the inflation device to the port 31, the device is actuated by the user to deliver a predetermined amount of fluid into the lumen 18, whereby the balloon 15 is expanded laterally a predetermined distance for vascular sealing purposes. The distal end of the hub 14 has an annular shaft connection bore 33. The shaft 13 is connected in the bore 33 by a suitable connection method. The hub 14 may be constructed of HDPE, polyimide, nylon stainless steel or a combination of such materials for example. The proximal end of the hub 14 has a threaded annular socket 25 for connectably receiving a cap 26. Although the shaft 13 and hub 14 are described herein as being connected, but separate structures, it is specifically within the purview of this invention that they may alternatively form a unitary, integrally formed structure.

The cap 26 has a cylindrical configuration of a predetermined diameter larger than that of the hub 14. A threaded mating end 27 is disposed on the distal end of the cap 26 for connection with the socket 25 of the hub 14. The cap 26 has a proximal access aperture 28 which defines an axial lumen that extends distally and is coextensive with the apparatus lumen 18 when operatively connected. The proximal access aperture 28 permits extension of the core wire 17 therethrough and into the apparatus lumen 18. When connected to the hub 14 and moved distally, the cap 26 connection end 25 engages an O-Ring 29 which is seated in the cap connection end 25 of the hub 14. Cap 26 engagement of the O-Ring 29 creates a seal in the lumen 18 around the core wire 17. Also, in the actuated state, the O-Ring 29 grips the core wire 17 and maintains it in a predetermined longitudinal position.

The balloon 15 is disposed near the distal end of the shaft 13. The balloon 15 body 36 is preferably a tubular structure in an uninflated state with a predetermined slightly tapered (distally) configuration. The balloon body 36 is connected to the shaft body 22 at its proximal end by heat bonding, adhesives or other known means. In an inflated state, the balloon 15 assumes a rounded configuration, preferably elliptical, with a minimum inflated diameter of greater than or equal to two times the french size of the puncture hole 57 being sealed. The height or thickness of the inflated balloon 15 is preferably less than one half the diameter of a typical blood vessel being sealed, so as to minimize obstruction of flow through the blood vessel. The balloon 15 body 36 is preferably constructed of an expandable material such as PE, PET, nylon, natural latex and the like.

The core wire 17 is rigid, elongated and disposed longitudinally in the lumen 18. The majority of the wire 17 has a predetermined, preferably uniform diameter of approximately 0.016 inches. Importantly, the wire 17 is tapered at a predetermined distal region. The proximal end of the wire 17 extends out of the proximal access aperture 28 of the cap 26, a predetermined distance. The core wire 17 is preferably constructed of stainless steel or nickel titanium alloys. Referring to FIGS. 3 and 4, during an inflation state, retraction of the core wire 17 constricts or compresses the balloon 15 causing it to expand laterally and shrink longitudinally to assume a flat, thin profile with a high sealing diameter. A marker band 45 of platinum or a similar radiopaque material is preferably connected at a predetermined position on the core wire 17 for position indication to the user. Alternatively, the marker band may be connected to the shaft 13. During a deflation state, the core wire 17 is extended distally by the user to longitudinally stretch the balloon 15 to its normal state and thereby shrink the lateral diameter of the balloon 15. This enables the uninflated balloon 15 to assume a low diameter or profile for apparatus 10 removal to minimize trauma to the blood vessel 56 and puncture site 57.

The flexible a traumatic tip or extension 16 is shown disposed at the distal end 12 of the vascular sealing device 10. The extension 16 preferably has a tubular structure with a diameter less than that of the uninflated balloon 15 and shaft 13. The extension 16 is formed of a flexible material, preferably coiled platinum wire. The tip 16 decreases the level of trauma to the vessel wall during insertion and manipulation of the device 10. The tip 16 is preferably slightly angled. The tip 16 has a rounded, solid end portion 38 to which is connected the core wire 17.

Referring to FIGS. 2–7, in use, the vascular sealing device 10 is pre-inserted into the input end 45 of a reaccess sheath 49 as shown in FIG. 2. The reaccess sheath 49 comprises an elongated shaft 52 with a tapered distal end 51 and an ingress/egress hub 50. The reaccess sheath 49 is preferably constructed of Teflon or a similarly lubricious material and fits tightly over the device 10.

As is shown in FIG. 5, the assembly of the uninflated vascular sealing device 10 and the reaccess sheath 49 is first inserted into a standard introducer or vascular sheath 61, which is of a known design and which has been previously positioned through a puncture 57 in the skin surface 58, tissue 59, vessel wall 60 and within a blood vessel 56 of a patient for performance of a medical intravascular procedure. Referring to FIG. 6, the assembly is advanced by manual manipulation until the distal end 12 extends just beyond the distal end of the introducer 61 and into the blood vessel 56. Fluid is then injected, via a known inflating means (not shown), into the device 10 through the inflation port 31 until a predetermined amount of balloon 15 inflation is attained as for example is shown in FIGS. 3 and 6. Next, the device 10 is manually pulled slightly proximally back through the introducer sheath 61 so that the balloon 15 abuts the distal end of the sheath 61. The core wire 17 is also manually proximally pulled to flatten the profile of the device 10 and minimize disturbance of blood flow in vessel 56. Referring to FIG. 7, the balloon 15 is manually proximally manipulated to effect a hemostatic seal at the blood vessel puncture site 57. Next, and importantly, a procoagulant is injected through a fluid access port 53 of the sheath 61 and is released out its distal end at the puncture site 57. The balloon section 15 remains abutted against the inner vessel wall 60 at the puncture site 57 while the introducer 61 may be retracted. After a predetermined time period, on the order of 1–3 minutes, the balloon 15 is deflated and the core wire 17 is advanced distally to decrease its profile for removal. The reaccess sheath 49 is advanced distally over the deflated balloon 15, as is shown in FIG. 4, and the combined device-sheath assembly may be pulled proximally out of the puncture site 57 along with the introducer 61. Alternatively, the vascular sealing apparatus 10 may be removed proximally away from the reaccess sheath 49, along with the introducer 61, leaving the sheath 49 in place for reaccess with a guide wire, for example. In the later case, the sheath 49 may be removed at a later time, with or without a guidewire remaining in place.

The procoagulant may include one of the following substances or combinations of substances: (1) thrombin, (2) collagen, (3) fibrin/fibrinogen, (4) cyanoacrylate, (5) thrombin and collagen, (6) fibrin/fibrinogen and collagen, (7) cyanoacrylate and collagen, and (8) thrombin and fibrin/fibrinogen.

The advantages of the device 10 and method of the present invention include, but are not limited to, both individually and cooperatively, (1) that the inflated balloon 15 blocks egress of blood immediately upon being properly positioned in the blood vessel at the puncture site to provide fast hemostasis; (2) that the inflated baboon 15 acts as an internal marker to permit the user to accurately gauge the depth of the puncture and the thickness of the tissues surrounding the puncture; and (3) that the inflated balloon 15 acts as a backstop at the inner wall of the blood vessel to (i) precisely position the sealing clot in the puncture and (ii) to prevent procoagulant from entering the patient's circulatory system.

Referring to FIGS. 8–11, an alternative embodiment of the vascular sealing device 66 is shown. The vascular sealing device 66 has proximal 67 and distal 68 ends. The vascular sealing device 66 generally comprises a body or shaft 69, an adapter or hub 70 disposed at the proximal end of the shaft 69, a balloon 71 portion disposed at the distal end of the shaft 69, and a tip 72 disposed at the distal end of the balloon 71. A core wire 73 is connected to the tip 72 and extends, internally, through a lumen 74 of the device 66 and out the proximal end 67.

The shaft 69 is rigid and has an elongated cylindrical or tubular configuration. The shaft 69 has a diameter, preferably uniform, less than the diameter of the access lumen of the introducer or sheath with which it is used, and a predetermined length. The lumen 74 extends the entire length of the shaft 69. The proximal end of the shaft 69 is connected to the hub 70. The distal end of the shaft 69 is connected to the balloon 71. The shaft 69, as well as the other components of this device 66 embodiment, is constructed of materials similar to those of device 10.

The hub 70 is rigid and has an generally cylindrical configuration. The proximal end of the shaft 69 is connected to the distal end of the hub. The proximal end of the hub 70 has a threaded annular socket for connectably receiving a cap 75. A hollow center or lumen extends from the proximal end of the hub 70, axially and distally, to communicatively connect with the lumen 74 of the shaft 69.

The hub 70 has an integral inflation port 77. The inflation port 77 has an interior, hemispherical inflation lumen 78 which extends into the shaft 69 and the balloon 71. The inflation lumen 78 is formed between the outer shaft wall 86 or layer and an inner shaft wall 87. The inner shaft 87 wall further surrounds and defines a portion of the access lumen 74. At the near distal end of the shaft 69, the inner wall 87 merges with the outer wall 86 to form a transition wall 89 at a predetermined distal hemispherical area. The inflation lumen 78 is completely independent of the access lumen 74. Upon connection of the inflation device to the port 77, the device is actuated by the user to deliver a predetermined amount of fluid into the lumen 78 and to the balloon 71, whereby the balloon 71 is expanded laterally a predetermined distance for vascular sealing purposes.

The hub 70 further has a integral injectate or introduction port 79. The injectate port 79 has an interior, hemispherical injectate lumen 80 which extends into the shaft 69 to a plurality of injectate egress apertures 81. The injectate lumen 80 is formed between the outer shaft wall 86 or layer and an inner shaft wall 87. The injectate lumen 80 is completely independent of the access lumen 74 and from the inflation lumen 78. The injectate apertures 81 are disposed in the outer wall 86, a predetermined distance from each other and from the balloon 71. A procoagulant is injected through the injectate port 79, into the injectate lumen 80, and is released at the puncture site 57 through the injectate apertures 81.

The cap 75 has a cylindrical configuration of a predetermined diameter larger than that of the hub 70. A threaded mating end of the cap 75 connects with the hub 70. The cap 75 has a proximal access aperture which permits extension of the core wire 73 therethrough and into the apparatus central access lumen 74. When connected to the hub 70 and moved distally, the cap 75 connection end engages an O-Ring 76 which is seated in the cap connection end of the hub 70. Cap 75 engagement of the O-Ring 76 creates a seal in the lumen 74 around the core wire 73. Also, in the actuated state, the O-Ring 76 grips the core wire 73 and maintains it in a predetermined longitudinal position. The balloon 71 is disposed near the distal end of the shaft 69. The balloon 71 body 88 is connected to the shaft outer wall 86 and to the transition wall 89, at its proximal end. The body 88 surrounds the distal end of the inner wall 87 to define the balloon 71, which is communicatively connected to the inflation lumen 78.

The core wire 73 is rigid, elongated, disposed longitudinally in the access lumen 74, and has a predetermined length. The majority of the wire 73 has a predetermined diameter with a tapered distal region. The proximal end of the wire 73 extends out of the proximal access aperture of the cap 75, a predetermined distance. The distal end of the wire 73 is connected to the tip 72. A radiopaque marker band 82 is connected at a predetermined position on the core wire 73 for position indication to the user. During a deflation state, the core wire 73 is extended distally by the user to longitudinally stretch the balloon 71 to its normal state and thereby shrink the lateral diameter of the balloon 71.

The flexible atraumatic tip or extension 72 is shown disposed at the distal end 68 of the vascular sealing device 66. The extension 72 preferably has a tubular structure with a diameter less than or equal to that of the uninflated balloon 71 and shaft 69.

FIG. 12, shows another alternative embodiment of the vascular sealing device 90. The vascular sealing device 90 generally comprises a body or shaft 91, a hub or adapter 92 disposed at the proximal end of the shaft 91, a balloon 93 portion disposed at the distal end of the shaft 91, and a tip 94 disposed at the distal end of the baboon 93. A core wire 95 is connected to the tip 94 and extends, internally, through a lumen 96 of the device 90. In this embodiment, balloon inflation fluid is injected in an adapter port 97 which is communicatively connected to the central lumen 96 and to the balloon 93 interior. Also in this embodiment, procoagulant is injected in adapter port 98 which is communicatively connected to an interior lumen 99 which has injectate apertures 100 disposed at predetermined positions proximally adjacent the balloon 93 on shaft 91.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof; including both structural equivalents and equivalent structures.

The invention claimed is:

1. A medical sealing apparatus for use in closing an opening in a blood vessel, comprising:

(a) a body structure having a proximal and a distal end, said body structure timber having an elongated tubular shaft with proximal and distal ends, an adapter connected to said proximal end of said shaft, and a central lumen extending axially through said shaft and said adapter;

(b) an inflatable member disposed adjacent said distal end of said shaft and communicatively connected to said lumen, said inflatable member having an inflated diameter and a deflated diameter which is less than that of said inflated diameter;

(c) means to introduce a procoagulant to the blood vessel opening at a point proximally located with respect to said inflatable member; and (d) means, connected to said body structure, to longitudinally compress said inflatable member so that it assumes a predetermined configuration during an inflation and to longitudinally stretch said inflatable member so that it returns to said deflated diameter subsequent to an inflation.

2. The medical sealing apparatus of claim 1, wherein said means to introduce a procoagulant is an introducer having an axial lumen opening to a distal insertion end adapted for location in the blood vessel opening, a fluid injection port being communicatively connected to said introducer lumen, said body structure shaft being extended through said introducer lumen so that said inflatable member is disposed outwardly beyond said introducer distal insertion end, procoagulant being introduced to said introducer lumen via said fluid injection port and distributed out said distal insertion end.

3. The medical sealing device of claim 1, wherein said means to introduce a procoagulant comprises a procoagulant introduction lumen disposed within said body structure, a procoagulant ingress port disposed on an exterior surface of said body structure and being communicatively connected to said introduction lumen, and at least one procoagulant egress aperture disposed at a predetermined location on said body structure and being communicatively connected to said introduction lumen.

4. The medical sealing device of claim 3, wherein said procoagulant introduction lumen extends axially through said body structure shaft and adapter, wherein said procoagulant ingress port is disposed on said adapter, and wherein said at least one procoagulant egress aperture is disposed on said shaft at a predetermined location relative to said inflatable member.

5. The medical sealing device of claim 1, wherein said means to longitudinally compress and stretch comprises an elongated wire member connected to said body structure shaft distal end and extending proximally through said central lumen and out a proximal aperture in said body structure adapter, said means to longitudinally compress and stretch further comprising means, disposed at said adapter proximal aperture, to lock said wire in a predetermined position.

6. The medical sealing device of claim 5, wherein said means to lock said wire comprises an O-Ring disposed at a predetermined position in said body structure adapter and annularly about said central lumen, and a compressive cap adjustably longitudinally compressing said O-Ring and urging said O-Ring into lateral frictional engagement with said wire in said central lumen.

7. The medical sealing device of claim 1, further comprising a sheath slidably disposed over said body structure shaft, said sheath having a proximal end, a distal end, and a predetermined length whereby said inflatable member extends beyond said distal end of said sheath, said sheath further having an inside dimension which is slightly greater than an outside dimension of said shaft.

8. The medical sealing device of claim 1, further comprising a radiopaque marker band disposed at a predetermined position on said body structure.

9. The medical sealing device of claim 1, further comprising a flexible tip structure connected to said distal end of said body structure shaft, distally with respect to said inflatable member.

10. The medical sealing device of claim 1, wherein said body structure adapter has an inflation port communicatively connected to said central lumen and wherein said central lumen is communicatively connected to said inflation member, whereby fluid is introduced in said inflation port and through said central lumen to inflate said inflation member.

11. The medical sealing device of claim 1, wherein said body structure adapter has an inflation port and a communicatively connected longitudinal inflation lumen, and wherein said inflation lumen is communicatively connected to said inflation member, whereby fluid is introduced in said inflation port and through said inflation lumen to inflate said inflation member.

12. The medical sealing device of claim 1, wherein said body structure adapter has an inflation port communicatively connected to said central lumen and wherein said central lumen is communicatively connected to said inflation member, whereby fluid is introduced in said inflation port and through said central lumen to inflate said inflation member, and wherein said means to introduce a procoagulant is an introducer having an axial lumen opening to a distal insertion end adapted for location in the blood vessel opening, a fluid injection port being communicatively connected to said introducer lumen, said body structure shaft being extended through said introducer lumen so that said inflatable member is disposed outwardly beyond said introducer distal insertion end, procoagulant being introduced to said introducer lumen via said fluid injection port and distributed out said distal insertion end, and wherein said inflatable member has an inflated diameter and a deflated diameter which is less than that of said inflated diameter, and wherein said device further comprises means to longitudinally compress said inflatable member so that it assumes a predetermined configuration during an inflation and to longitudinally stretch said inflatable member so that it returns to said deflated diameter subsequent to an inflation, and wherein said device further comprises a sheath slidably disposed over said body structure shaft, said sheath having a proximal end, a distal end, and a predetermined length whereby said inflatable member extends beyond said distal end of said sheath, said sheath further having an inside dimension which is slightly greater than an outside dimension of said shaft.

13. The medical sealing device of claim 1, wherein said body structure adapter has an inflation port and a communicatively connected longitudinal inflation lumen, and wherein said inflation lumen is communicatively connected to said inflation member, whereby fluid is introduced in said inflation port and through said inflation lumen to inflate said inflation member, and wherein said means to introduce a procoagulant comprises a procoagulant introduction lumen disposed within said body structure, a procoagulant ingress port disposed on an exterior surface of said body structure and being communicatively connected to said introduction lumen, and at least one procoagulant egress aperture disposed at a predetermined location on said body structure and being communicatively connected to said introduction lumen, and wherein said inflatable member has an inflated diameter and a deflated diameter which is less than that of said inflated diameter, and wherein said device further comprises means to longitudinally compress said inflatable member so that it assumes a predetermined configuration during an inflation and to longitudinally stretch said inflatable member so that it returns to said deflated diameter subsequent to an inflation.

14. The medical sealing device of claim 1, wherein said body structure adapter has an inflation port communicatively connected to said central lumen and wherein said central lumen is communicatively connected to said inflation member, whereby fluid is introduced in said inflation port and through said central lumen to inflate said inflation member, and wherein said means to introduce a procoagulant comprises a procoagulant introduction lumen disposed within said body structure, a procoagulant ingress port disposed on an exterior surface of said body structure and being communicatively connected to said introduction lumen, and at least one procoagulant egress aperture disposed at a predetermined location on said body structure and being communicatively connected to said introduction lumen, and wherein said inflatable member has an inflated diameter and a deflated diameter which is less than that of said inflated diameter, and wherein said device further comprises means to longitudinally compress said inflatable member so that it assumes a predetermined configuration during an inflation and to longitudinally stretch said inflatable member so that it returns to said deflated diameter subsequent to an inflation.

15. A method for closing a puncture or other opening in a blood vessel, comprising the steps of:
  (a) inserting a balloon apparatus through an introducer which is disposed in the blood vessel opening;
  (b) inflating said balloon apparatus;
  (c) moving said balloon apparatus into contact with the opening;
  (d) introducing a procoagulant to the opening;
  (e) deflating said balloon apparatus; and
  (f) removing said balloon apparatus through the opening.

16. The method of claim 15, wherein said procoagulant is injected through the introducer.

17. The method of claim 15, wherein said procoagulant is injected through the balloon apparatus.

18. The method of claim 15, further comprising the steps of configuring said balloon apparatus by compressing said balloon apparatus subsequent to inflating said balloon apparatus, and of configuring said balloon apparatus by stretching said balloon apparatus prior to removing said balloon apparatus.

19. A medical sealing apparatus for use in closing an opening in a blood vessel, comprising:

(a) a body structure having a proximal and a distal end, said body structure further having an elongated tubular shaft with proximal and distal ends, an adapter connected to said proximal end of said shaft, and a central lumen extending axially through said shaft and said adapter;

(b) an inflatable member disposed adjacent said distal end of said shaft and communicatively connected to at least one said lumen; and (c) means to introduce a procoagulant to the blood vessel opening at a point proximally located with respect to said inflatable member, and wherein said body structure adapter has an inflation port communicatively connected to said central lumen and wherein said central lumen is communicatively connected to said inflation member, whereby fluid is introduced in said inflation port and through said central lumen to inflate said inflation member, and wherein said means to introduce a procoagulant is an introducer having an axial lumen opening to a distal insertion end adapted for location in the blood vessel opening, a fluid injection port being communicatively connected to said introducer lumen, said body structure shaft being extended through said introducer lumen so that said inflatable member is disposed outwardly beyond said introducer distal insertion end, procoagulant being introduced to said introducer lumen via said fluid injection port and distributed out said distal insertion end, and wherein said inflatable member has an inflated diameter and a deflated diameter which is less than that of said inflated diameter, and wherein said device further comprises means, connected to said body structure, to longitudinally compress said inflatable member so that it assumes a predetermined configuration during an inflation and to longitudinally stretch said inflatable member so that it returns to said deflated diameter subsequent to an inflation, and wherein said device further comprises a sheath slidably disposed over said body structure shaft, said sheath having a proximal end, a distal end, and a predetermined length whereby said inflatable member extends beyond said distal end of said sheath, said sheath further having an inside dimension which is slightly greater than an outside dimension of said shaft.

20. A medical sealing apparatus for use in closing an opening in a blood vessel, comprising:

(a) a body structure having a proximal and a distal end, said body structure further having an elongated tubular shaft with proximal and distal ends, an adapter connected to said proximal end of said shaft, and a central lumen extending axially through said shaft and said adapter;

(b) an inflatable member disposed adjacent said distal end of said shaft and communicatively connected to at least one said lumen; and (c) means to introduce a procoagulant to the blood vessel opening at a point proximally located with respect to said inflatable member, and wherein said body structure adapter has an inflation port and a communicatively connected longitudinal inflation lumen, and wherein said inflation lumen is communicatively connected to said inflation member, whereby fluid is introduced in said inflation port and through said inflation lumen to inflate said inflation member, and wherein said means to introduce a procoagulant comprises a procoagulant introduction lumen disposed within said body structure, a procoagulant ingress port disposed on an exterior surface of said body structure and being communicatively connected to said introduction lumen, and at least one procoagulant egress aperture disposed at a predetermined location on said body structure and being communicatively connected to said introduction lumen, and wherein said inflatable member has an inflated diameter and a deflated diameter which is less than that of said inflated diameter, and wherein said device further comprises means, connected to said body structure, to longitudinally compress said inflatable member so that it assumes a predetermined configuration during an inflation and to longitudinally stretch said inflatable member so that it returns to said deflated diameter subsequent to an inflation.

21. A medical sealing apparatus for use in closing an opening in a blood vessel, comprising:

(a) a body structure having a proximal and a distal end, said body structure further having an elongated tubular shaft with proximal and distal ends, an adapter connected to said proximal end of said shaft, and a central lumen extending axially through said shaft and said adapter;

(b) an inflatable member disposed adjacent said distal end of said shaft and communicatively connected to at least one said lumen; and (c) means to introduce a procoagulant to the blood vessel opening at a point proximally located with respect to said inflatable member, and wherein said body structure adapter has an inflation port communicatively connected to said central lumen and wherein said central lumen is communicatively connected to said inflation member, whereby fluid is introduced in said inflation port and through said central lumen to inflate said inflation member, and wherein said means to introduce a procoagulant comprises a procoagulant introduction lumen disposed within said body structure, a procoagulant ingress port disposed on an exterior surface of said body structure and being communicatively connected to said introduction lumen, and at least one procoagulant egress aperture disposed at a predetermined location on said body structure and being communicatively connected to said introduction lumen, and wherein said inflatable member has an inflated diameter and a deflated diameter which is less than that of said inflated diameter, and wherein said device further comprises means, connected to said body structure, to longitudinally compress said inflatable member so that it assumes a predetermined configuration during an inflation and to longitudinally stretch said inflatable member so that it returns to said deflated diameter subsequent to an inflation.

* * * * *